United States Patent [19]

Dawson

[11] Patent Number: 5,797,406
[45] Date of Patent: Aug. 25, 1998

[54] CIGARETTE MANUFACTURE

[75] Inventor: John Dawson, High Wycombe, England

[73] Assignee: Molins PLC, Bucks, Great Britain

[21] Appl. No.: 737,581

[22] PCT Filed: May 19, 1995

[86] PCT No.: PCT/GB95/01142

§ 371 Date: Nov. 18, 1996

§ 102(e) Date: Nov. 18, 1996

[87] PCT Pub. No.: WO95/31908

PCT Pub. Date: Nov. 30, 1995

[30] Foreign Application Priority Data

May 19, 1994 [GB] United Kingdom ............. 9410013
Oct. 1, 1994 [GB] United Kingdom ............. 9419810

[51] Int. Cl.$^6$ .................................................. A24C 5/14
[52] U.S. Cl. .................... 131/84.1; 131/84.2; 131/84.4; 131/281
[58] Field of Search ............................ 131/84.1, 84.2, 131/84.3, 84.4, 281, 905, 108

[56] References Cited

U.S. PATENT DOCUMENTS 4,785,830 11/1988 Moller et al. ..................... 131/84.1
4,865,052 9/1989 Hartmann et al. ................ 131/844

*Primary Examiner*—Vincent Millin
*Assistant Examiner*—Charles W. Anderson
*Attorney, Agent, or Firm*—Antonelli, Terry, Stout, & Kraus,LLP

[57] ABSTRACT

A scanning device for a cigarette making machine comprises a low energy X-ray beam emitter (110) for passing an X-ray beam through the cigarette rod (116), and an X-ray detector (126;202) arranged to receive the beam after it has passed through the cigarette rod and to produce an output signal which can be amplified and fed to a control circuit (130) for the cigarette making machine.

13 Claims, 2 Drawing Sheets

CIGARETTE MANUFACTURE

In the manufacture of cigarettes it is common to use a nucleonic device for scanning the finishing cigarette rod, usually before it is cut into individual rod lengths, to enable cigarette weights to be controlled by means of a trimming device which removes a variable proportion of the tobacco stream forming the cigarette filler. The rod weight signal can also be used to enable underweight cigarettes or cigarettes with pronounced voids to be ejected further downstream, usually in the filter attachment machine. The use of nucleonic scanning devices for these purposes has been common in the cigarette industry for many years.

This invention is based partly on an appreciation that a low-energy X-ray beam of the type described (which for convenience will be referred to as an X-ray beam) can be used safely in the environment of a cigarette making machine and produces a satisfactory weight signal when used in combination with a photodiode detector with a height approximately equal to the diameter of a cigarette rod. Low-energy X-ray sources have become available as proprietary items. Previously available higher-energy sources were not suitable for cigarette scanning, mainly because the predominately higher frequencies penetrated too readily to give a useful rod weight signal. A low energy X-ray source, on the other hand, can be used in combination with a photodiode by which a beam about the same height as, or slightly less than, the diameter of the cigarette rod can be received and monitored to provide a signal averaging the rod density across its diameter; the reference here to the height of the beam is based on the assumption that the beam is directed horizontally through the rod, though the beam may alternatively, for example, be vertical.

The use of an X-ray beam system for scanning a cigarette rod is disclosed in British patent specification No. 2133965. That specification discusses the possibility of scanning, by means of an X-ray beam, either the completed cigarette rod or the cigarette filler stream before it is enclosed in a wrapper web to form a rod. For both purposes the patent applicant assumes that the strength of the X-ray beam can be maintained precisely. However, we have discovered that, for precise control of the weights of cigarettes, it would be very difficult and very expensive to maintain the voltage applied to the X-ray beam emitter with sufficient accuracy to achieve a satisfactory result. Moreover, we have found that temperature variations of the X-ray beam detector can have a significant effect on the output signal of the detector, and we have found it important to provide a second or reference detector to compensate for temperature variations of the main detector.

According to the present invention, a scanning device for a cigarette making machine comprises a low energy X-ray beam emitter for passing an X-ray beam through the cigarette rod and towards a photodiode or other plate-like X-ray detector which produces an output signal responsive to the strength of the X-ray beam reaching the detector, which signal is fed to a control circuit for the cigarette making machine, characterised in that the scanning device includes a reference detector of similar type to the first-mentioned detector, that both detectors are mounted on a heat-conducting member whereby they are maintained at substantially the same temperature, and that outputs from both detectors are fed to the control circuit, which is arranged to compensate for temperature-induced variations in the output from the first detector by reference to the output from the second detector.

The second (reference) detector is preferably substantially identical to the first detector, and the two detectors are mounted symmetrically with respect to the axis of the X-ray beam so that equal beam strengths are directed towards the two detectors. Thus the output from the second detector can compensate not only for variations in the temperature of both detectors, but also for variations which inevitably occur in the beam strength of the X-ray emitter as a result of applied voltage variations.

Reference is made above to a low-energy X-ray beam emitter. By way of explanation, commonly available X-ray tubes until fairly recently were intended to operate at an energy level of tens or hundreds of Kilovolts, (depending on the applied definition of X-rays). A suitably low energy source usable in the present invention, on the other hand, has an energy level of a different order of magnitude, namely approximately 13 Kilovolts, which results in frequencies up to that represented by a wavelength of approximately 1 Angstrom. We at present believe that a suitable energy level is in the range 6–20 Kilovolts and is preferably in the range 10–16 Kilovolts.

Examples of a cigarette making machine and of cigarette rod scanning systems according to this invention are shown diagrammatically in the accompanying drawings. In these drawings.

Figure 1:
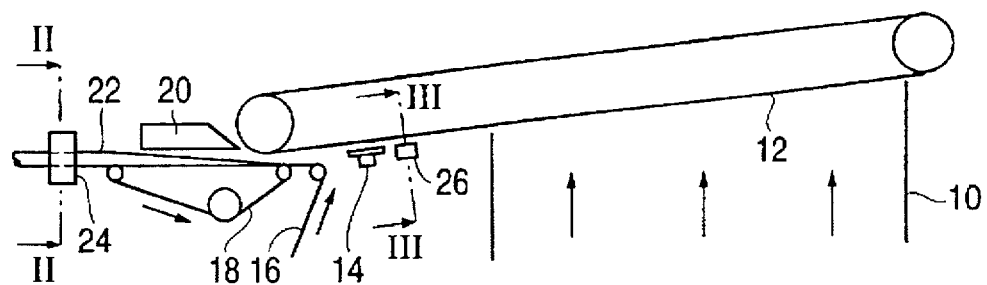
FIG. 1 is a front view of part of a complete cigarette making machine.

FIG. 1 shows diagrammatically a conventional Molins-type cigarette making machine in which a cigarette filler stream is formed by showering tobacco up a chimney 10 towards a suction band 12. Part of the filler stream is removed by a trimmer 14 which is vertically movable in any well known manner to control the weight per unit length of the finished cigarette rod; alternatively, the trimmer may be in a fixed position and the band, in the region of the trimmer, may be moved up and down. The portion of the cigarette filler stream remaining on the band 12 following the trimmer 14 is enclosed in a continuous wrapper web 16 with the aid of a garniture tape 18 and a cooperating upper assembly 20 by which the filler stream is finally shaped so that the wrapper web 16 can be sealed around it to form a finished cigarette rod 22. A scanning device 24 scans the cigarette rod and controls the vertical position of the trimmer 14.

An additional position control for the trimmer is provided by a scanning device 26 immediately upstream (or alternatively immediately downstream) of the trimmer 14. The device 26 provides a quick response to changes in the density of the tobacco forming the filler stream, while accurate long-term control of the weights of finished cigarettes is provided more particularly by the scanning device 24. The use of dual scanning devices is know per se: the Molins Mark 8 cigarette making machine used a pneumatic device as a quick scanner in combination with a nucleonic scanning device scanning the completed cigarette rod (see for example U.S. Pat. No. 3,089,497).

The cigarette scanning device 24 is preferably an X-ray device according to this invention, and the filler stream scanning device 26 is preferably either an infrared device (as shown) or a simpler/cheaper form of low-energy X-ray device which may be powered by the same power supply as the device 24. These devices are shown more fully in FIGS.

2 and 3 respectively. However, these devices may in principle be interchanged.

Figure 2:
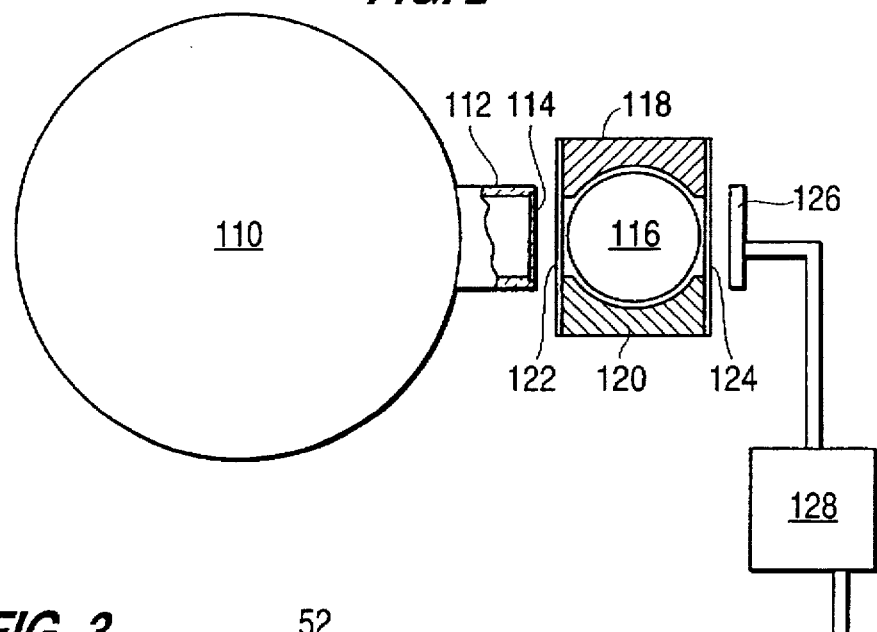
FIG. 2 is an enlarged cross-section on the line II—II in FIG. 1.

With reference to FIG. 2, an X-ray tube 110 is provided to emit an X-ray beam through an outlet 112 including a window member 114 which is transparent to the X-rays (e.g. beryllium) buy may include a mask (not shown) causing the cross-sectional outline of the beam to be rectangular. The beam emitted through the window 114 has a height slightly less than the diameter of a cigarette rod 116 which is guided by a rod guiding device comprising upper and lower members 118 and 120 and side windows 122 and 124 of titanium or other material (e.g. aluminium) through which the X-ray beam can pass. What remains of the beam, as a result of variable attenuation by the cigarette rod, impinges on a photodiode 126 which may be silicon-based and has a height approximately equal to the cigarette diameter. A signal from the photodiode passes to an amplifier 128 from which a rod density signal is transmitted to a control circuit 130 of a basically known type by which control operations, for example trimming as described above, are achieved.

The X-ray beam may have a width, in the direction of the cigarette axis, which is less than the diameter of the cigarette, for example 6 mm or possibly as little as 3 mm. The photodiode 126 has a similar width measured in the direction of the cigarette axis, so as to receive substantially the entire beam that has passed through the cigarette rod.

It should be noted that the rod guiding members 118 and 120 have suitably concave rod guiding surfaces which have a width, measured in the direction of the beam, sufficient to guide the rod with reasonable accuracy horizontally as well as vertically.

In nucleonic scanning systems commonly used until now, it has been common to use narrower rod guide members (measured in the direction of the beam) so as to allow the height of the beam to be almost equal to the cigarette diameter. This is believed to have been considered necessary because of the relatively low energy level of the nucleonic beams commonly used. As a result, it has been necessary to make provision for different rod guide devices to be used for slightly varying rod diameters. The higher flux level available in accordance with the present invention, combined with the essentially different nature (wave energy) of an X-ray beam, allows the use of wider rod guide members 116 and 118. As a result the height of the beam that passes through the cigarette rod may be somewhat less than the cigarette diameter, but that can be tolerated because of the energy level being sufficient to produce an adequate signal, and the benefit in this lies in the fact that a given rod guide device can be used for a wider range of cigarette diameters since the resulting scanning signal is not so sensitive to the precise vertical position of the rod axis as the beam passes only through the wider part of the rod.

Power is supplied to the X-ray tube only while the cigarette making machine is in operation and a rod is passing through the rod guide 118,120. For example, a transducer may be used to detect the presence of the cigarette rod in or near the rod guide and to control an interlock so that power can be transmitted to the X-ray tube only during the presence of a cigarette rod.

A silicon photodiode may be sensitive to temperature. To eliminate any temperature effect, a similar second photodiode may be bonded to the photodiode 126 in back-to-back arrangement, possibly with an interposed layer of copper to ensure good heat conductivity and to ensure that X-rays do not pass through the first photodiode (the measurement photodiode) and enter the second photodiode. The output from the two photodiodes can then be connected to a differential electrical circuit whereby the temperature-related element of the photodiode 126 signal is cancelled by an identical signal from the second photodiode.

In addition to the back-to-back arrangement for temperature compensation (or as an alternative) the temperature of the photodiode or photodiodes may be controlled by a controllable cooling element encapsulated with the photodiode(s). For control purposes the temperature of the photodiode(s) may be detected by means of a platinum or nickel resistance thermometer or a thermistor or other semiconductor device bonded to the photodiode(s).

The photodiode 126 may be replaced by a vertical array of narrower photodiodes (measured vertically) each of which thus receives a portion of the beam passing through a different "slice" of the cigarette rod. The control circuit may compensate for the fact that the "slices" above and below the central one become progressively narrower (measured in the direction of the beam) and thus absorbs less of the beam. By this means, density differences in the cigarette rod at different levels can be monitored. Moreover, the signal from each element of the photodiode array can be monitored to detect the presence of a foreign body which is more opaque to the beam than is the tobacco. Cigarettes including foreign bodies detected in this way can be subsequently ejected in any known manner. The advantage in this case is that a relatively small foreign body lying in only one or possibly two "slices" of the cigarette rod can be more reliably detected than in prior systems in which the foreign body could only be detected if it had a detectable effect on the total beam passing through the entire height of the cigarette rod.

The X-ray tube may have a tungsten target, as commonly used. Alternatively, the target may be of a different material, for example copper, producing a lower "characteristic frequency".

The moisture content of the tobacco may be detected by any known means to provide a compensation signal which is fed to the control circuit 130.

The enhanced resolution of an X-ray scanning system according to this invention, compared with existing nucleonic scanners, may be used to detect and reject cigarettes with a low-density filling in a region at which the cigarette rod is cut, either in the cigarette maker or in the filter assembly machine: such cigarettes are liable to have poor quality ends.

Figure 3:
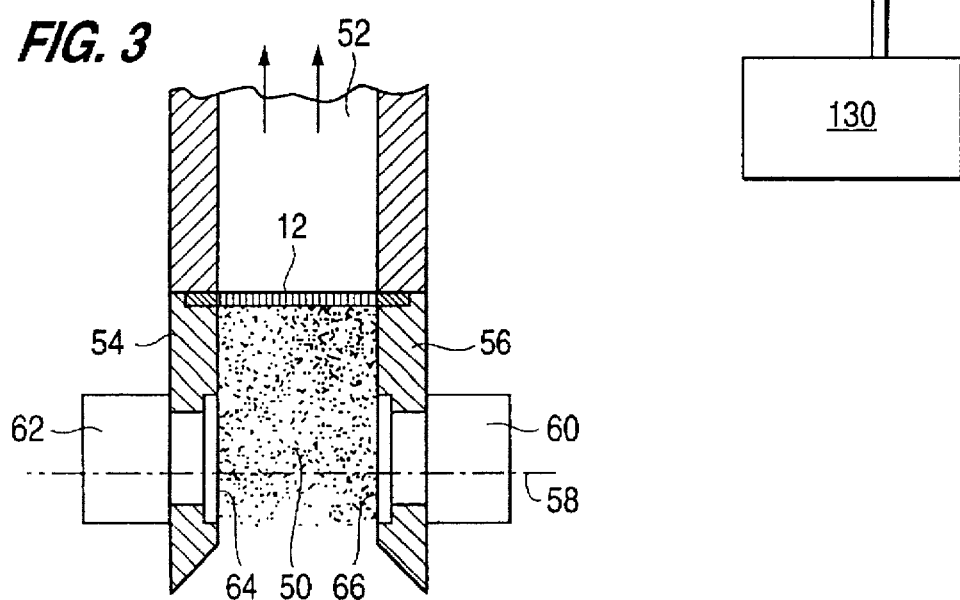
FIG. 3 is an enlarged cross-section on the line III—III in FIG. 1.

FIG. 3 illustrates diagrammatically the scanning device 26 which scans the cigarette filler stream before trimming. At this stage, the filler stream 50 is carried by the band 12, as mentioned above, with the aid of suction transmitted through the band 12 from a suction chamber 52. Side rails 54 and 56 confine the sides of the filler stream. A line 58 represents the average level at which the filler stream is subsequently trimmed by the trimmer 14.

The scanning device 26 (what may be termed a "feed-forward scanner") comprises an infrared source 60 which transmits an infrared beam (possibly via a group of optical fibres) horizontally through the filler stream 50 and towards an infrared detector 62. The rails 54 and 56 have apertures for this purpose which are sealed on the inner faces of the rails by transparent windows 64 and 66. It should be noted that the infrared beam in transmitted through the tobacco stream at approximately the level 58 at which the filler stream is subsequently trimmed. Alternatively, however, the infrared beam may be transmitted through the tobacco stream at a higher or lower level, or may extend across the full height of the tobacco stream between the band 12 and the line 58.

An alternative to an infrared device for feed-forward scanning might be an optical device measuring simply the height of the filler stream.

Any suitable electro-mechanical arrangement may be used for controlling the position of the trimmer 14 in response to both the rapid feed-forward signal from the infrared device 26 and the rod weight signal received from the X-ray scanning device.

Figure 4:
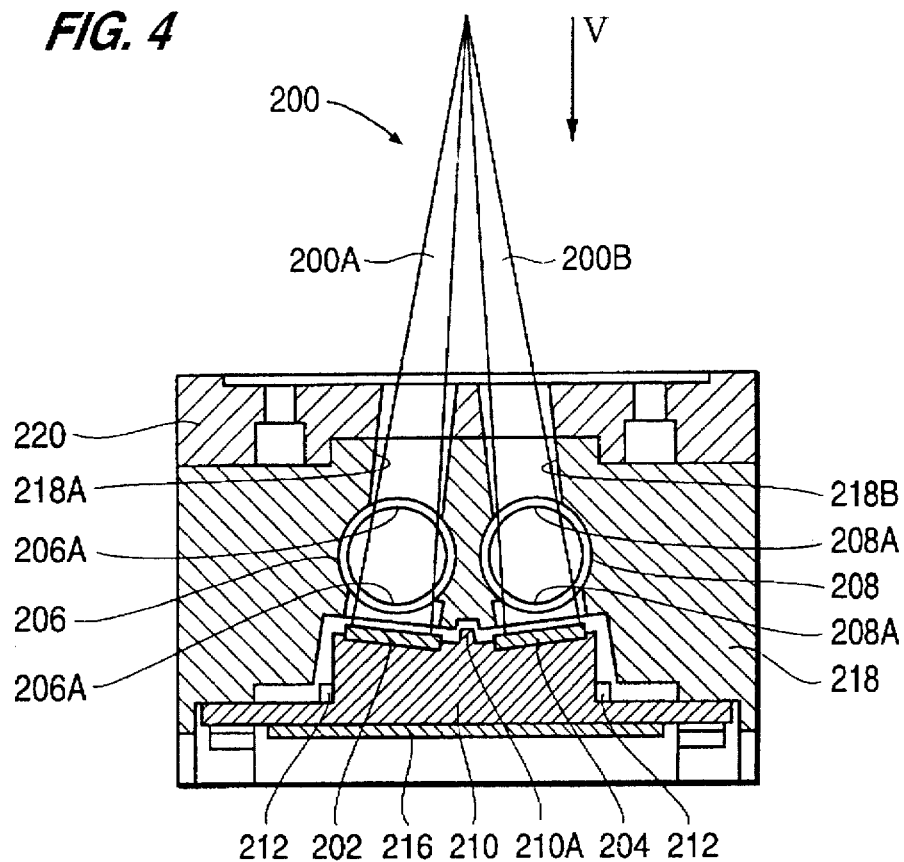
FIG. 4 is a cross-section in a vertical plane of a different X-ray device.

FIG. 4 shows a different X-ray scanning device by which a low-energy X-ray beam 200 from an X-ray tube (not shown) is directed towards two photodiodes 202 and 204 which may be in this case be identical to one another. Portions 200A and 200B of the X-ray beam 200 are shown separately, though the beam emitted from the X-ray tube is not divided.

The beam 200A passes through a tube 206 for guiding a cigarette rod, while the beam 200B passes through a similar tube 208 containing a reference beam absorption member or what may be termed a "reference cigarette" (not shown) which may comprise, for example, a hollow nylon tube designed to have a beam absorption characteristic similar to the average for the cigarette rod. The tubes 206 and 208 have titanium covered windows 206A and 208A which each have a width W (measured in the direction of the cigarette rod axis) which in this example is less than the cigarette diameter.

Each of the photodiodes 202,204 is mounted on a temperature-controlled aluminium member 210 so as to be normal to the axis of the respective beam 200A or 200B. For the purpose of controlling the temperature of the member 210 and hence of the photodiodes, there are two heating strips 212 the power to which is controlled by a temperature sensor 214 mounted in or adjacent to one side of the member 210. An amplifier circuit (of any known kind) for amplifying the output signals from the photodiodes is incorporated in a board 216 which is mounted on the back of the member 210 so as to be at a controlled temperature to ensure stability of operation of the amplifier.

The tubes 206,208 are mounted in a stainless steel block 218 which has suitably inclined bores 218A,218B to allow the passage of the beams 200A,200B. Extensions of the bores are provided in a member 220 which is secured to the block 218 and serves as a mounting for the X-ray tube (not shown).

A ridge 210A on the member 210 serves as a barrier preventing scatter of X-rays from either beam to the other photodiode.

Figure 5:
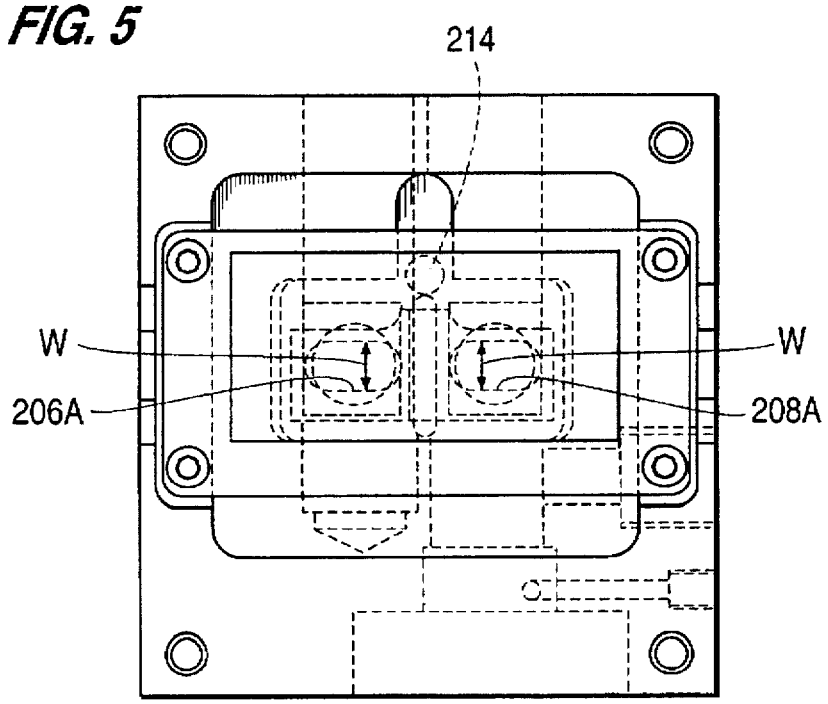
FIG. 5 is a view in the direction of the arrow V in FIG. 4.

The scanning device shown in FIGS. 4 and 5 has a vertically directed X-ray beam, but its orientation may be changed so that the beam is horizontal. However, for scanning the two cigarette rods in a twin-track cigarette making machine a vertically directed beam is appropriate. For this purpose, portions of the beam from a single X-ray tube may be directed towards three photodiodes: the outer portions via the two cigarette rods (assuming these are horizontally spaced) and the centre portion via a reference cigarette. Alternatively, four quadrants of the X-ray beam (as viewed in a cross-section through the beam) may be directed towards four photodiodes two of which (e.g. opposite quadrants) are associated with the two cigarette rods and the other two providing reference signals for the respective cigarette rods. This arrangement would ensure, if desired or necessary, that the intensities of the portions of the beam directed towards the four photodiodes are equal. For this purpose it is possible to use a beam cone from the X-ray tube of up to 40° cone angle.

In both of the above-described X-ray scanning devices, the X-ray tube may be a Lohmann ABE160, and may be powered by a switch mode power supply, operating at 100–200 Kilocycles. The heating strips 214 (FIG. 4) may be semiconductor devices of the type having a proportional integral differential controller so as to be capable of producing a variable heat output. The photodiodes may be large-area PIN Silicon photodiodes, an example of which is available from Graseby GK Intertest Ltd. (their part No. ST0029).

I claim:

1. A scanning device for a cigarette making machine, comprising a low-energy X-ray beam emitter for passing an X-ray beam through the cigarette rod and towards a first X-ray detector which produces an output signal responsive to the strength of the X-ray beam reaching the detector, which signal is fed to a control circuit for the cigarette making machine, characterised in that the scanning device includes a second X-ray detector as a reference detector, that both detectors are mounted on a heat-conducting member whereby they are maintained at substantially the same temperature, and that outputs from both detectors are fed to the control circuit, which is arranged to compensate for temperature-induced variations in the output from the first detector by reference to the output from the second detector.

2. A scanning device according to claim 1, in which the two detectors are mounted together in a back-to-back arrangement.

3. A scanning device according to claim 1, including means for detecting the temperature of the member on which the detectors are mounted, and means for cooling or heating the detector-mounting member in order to maintain the temperature of that member substantially constant.

4. A scanning device according to claim 1, in which the two detectors are mounted adjacent to one another and receive portions of the same X-ray beam, the portion of the X-ray beam which reaches the second detector being arranged to pass through a reference beam absorption member.

5. A scanning device according to claim 4, in which the two detectors are mounted symmetrically about the axis of the X-ray beam so that equal-strength portions of the X-ray beam are directed towards the respective detectors, and in which the reference beam absorption member has a beam absorption characteristic similar to that of an average cigarette rod.

6. A scanning device according to claim 4, in which the control circuit comprises a board which incorporates an amplifier circuit and is mounted on the back of the detector-mounting member.

7. A scanning device according to claim 1, in which the control circuit is arranged to control the trimming of the cigarette filler stream before it is enclosed in a wrapper to form a continuous cigarette rod, and in which trimming is also controlled in response to a signal from a second X-ray device or an infrared or other scanning device arranged to scan the filler stream before trimming takes place.

8. A device according to claim 1 for use in a cigarette making machine producing two parallel cigarette rods, in which portions of the beam from a single X-ray beam emitter are arranged to pass through the respective rods.

9. A scanning device according to claim 8, in which each of four quadrants of the X-ray beam, as viewed in a cross-section through the beam, is directed either towards an X-ray detector via one of the two cigarette rods, or towards an X-ray detector serving to provide a reference signal in association with the detector for one of the cigarette rods.

10. A scanning device for a cigarette making machine, comprising a low energy X-ray beam emitter for passing an X-ray beam through the cigarette rod and towards an X-ray detector which produces an output signal responsive to the strength of the X-ray beam reaching the detector, which signal is fed to a control circuit for the cigarette making machine, characterised in that the device includes a reference detector which receives a portion of the X-ray beam and is arranged to produce an output which is also connected to the control circuit, the beam directed towards the reference detector being arranged to pass through a reference beam absorption member having approximately the same beam absorption characteristic as a cigarette rod.

11. A scanning device according to claim 10, in which the first-mentioned detector and the reference detector are symmetrically positioned with respect to the axis of the X-ray beam.

12. A scanning device according to claim 10, in which the first-mentioned detector and the reference detector are photodiodes.

13. A scanning device according to claim 1, in which the first and second X-ray detectors are photodiodes.

* * * * *